(12) United States Patent
Canfield et al.

(10) Patent No.: US 12,207,917 B2
(45) Date of Patent: *Jan. 28, 2025

(54) ADAPTIVE ULTRASOUND SCANNING

(71) Applicant: KONINKLIJKE PHILIPS N.V., Eindhoven (NL)

(72) Inventors: Earl M. Canfield, New Braunfels, TX (US); Man Nguyen, Melrose, MA (US); Hua Xie, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/388,209

(22) Filed: Nov. 9, 2023

(65) Prior Publication Data

US 2024/0074675 A1 Mar. 7, 2024

Related U.S. Application Data

(63) Continuation of application No. 17/048,169, filed as application No. PCT/EP2019/059208 on Apr. 11, 2019, now Pat. No. 11,850,038.

(Continued)

(51) Int. Cl.
*A61B 5/107* (2006.01)
*A61B 8/08* (2006.01)
*G06T 7/00* (2017.01)
*G16H 50/30* (2018.01)

(Continued)

(52) U.S. Cl.
CPC ............ *A61B 5/107* (2013.01); *A61B 8/5223* (2013.01); *G06T 7/0012* (2013.01); *G16H 50/30* (2018.01);

(Continued)

(58) Field of Classification Search
CPC ........ G06N 20/00; G06N 3/045; G06N 3/044; G06N 3/088; G06N 3/02; G06V 10/82;

(Continued)

(56) References Cited

U.S. PATENT DOCUMENTS 6,149,594 A * 11/2000 Rock ............... A61B 8/065
600/437
6,443,896 B1 9/2002 Detmer
(Continued)

FOREIGN PATENT DOCUMENTS

DE 102015218531 A1 3/2017

OTHER PUBLICATIONS

Baumgartner et al: "Real-Time Standard Scan Plane Detection and Localization in Fetal Ultrasound Using Fully Convolutional Neural Networks"; Lecture Notes in Computer Science, 2016.
(Continued)

*Primary Examiner* — Aaron W Carter
*Assistant Examiner* — Courtney Joan Nelson

(57) ABSTRACT

The present disclosure describes imaging systems configured to generate adaptive scanning protocols based on anatomical features and conditions identified during a prenatal scan of an object. Systems may include an ultrasound transducer configured to acquire echo signals responsive to ultrasound pulses transmitted toward a target region. Processors coupled with the transducer can generate an image frame from the echoes and provide the image frame to a first neural network. The first neural network may be configured to identify an anatomical feature in the image frame. An indication of the anatomical feature may be provided a second neural network. The second neural network may then determine an anatomical measurement to be obtained based, in part, on the feature identified. The processors may be further configured to cause an indicator of the anatomical measurement to be obtained to be displayed on a user interface.

20 Claims, 8 Drawing Sheets

Related U.S. Application Data

(60) Provisional application No. 62/660,332, filed on Apr. 20, 2018.

(52) U.S. Cl.
CPC ... *A61B 8/0866* (2013.01); *G06T 2207/10132* (2013.01); *G06T 2207/20084* (2013.01); *G06T 2207/30044* (2013.01)

(58) Field of Classification Search
CPC ............. G06V 10/764; G06V 10/7715; G06V 2201/03; G06V 30/19173; G06V 20/64; G06V 30/194; G06V 10/806; G06T 7/0012; G06T 2207/30004; G06T 2207/20084; G06T 2207/10132; G06T 2207/30044; G06T 7/73; G06T 2200/04; A61B 1/000094; A61B 1/000096; A61B 5/7267; A61B 5/0013; A61B 2576/00; A61B 5/107; A61B 2034/105; A61B 2576/02; A61B 8/5223; A61B 8/0866; G16H 50/30
See application file for complete search history.

(56) References Cited

U.S. PATENT DOCUMENTS

| | | | |
|---|---|---|---|
| 6,530,885 B1 | 3/2003 | Entrekin et al. | |
| 8,556,814 B2 | 10/2013 | Monteiro de Barros Carneiro et al. | |
| 2009/0009371 A1 | 4/2009 | Carneiro et al. | |
| 2009/0093717 A1* | 4/2009 | Carneiro | G16H 50/30 600/443 |
| 2009/0270732 A1 | 10/2009 | Abe et al. | |
| 2010/0217123 A1 | 8/2010 | Eran et al. | |
| 2016/0000401 A1 | 1/2016 | Mienkina | |
| 2016/0038122 A1 | 2/2016 | Lee et al. | |
| 2016/0081659 A1 | 3/2016 | Perrey et al. | |
| 2016/0151041 A1* | 6/2016 | Lee | A61B 8/0866 600/440 |
| 2017/0000453 A1 | 1/2017 | Feltovich et al. | |
| 2017/0238909 A1 | 8/2017 | Shin et al. | |
| 2017/0273663 A1 | 9/2017 | Baym et al. | |
| 2017/0360411 A1* | 12/2017 | Rothberg | G06T 7/70 |
| 2017/0360412 A1 | 12/2017 | Rothberg et al. | |
| 2018/0042578 A1* | 2/2018 | Anand | A61B 8/465 |

OTHER PUBLICATIONS

International Search Report and Written Opinion for PCT/EP2019/059208, Mailing date: Jun. 5, 2019, 12 pages.

Jang, J. et al., "Automatic Estimation of Fetal Abdominal Circumference From Ultrasound Images," IEEE Journal of Biomedical and Health Informatics, 2017, vol. 22, No. 5, pp. 1512-1520.

* cited by examiner

ADAPTIVE ULTRASOUND SCANNING

CROSS-REFERENCE TO RELATED APPLICATIONS

This application is a continuation of U.S. patent Ser. No. 17/048,169, filed Oct. 16, 2020, which in turn is the U.S. National Phase application under 35 U.S.C. § 371 of International Application No. PCT/EP2019/059208, filed on Apr. 11, 2019, which claims the benefit of Provisional Application Ser. No. 62/660,332, filed Apr. 20, 2018, all of which are hereby incorporated by reference herein.

TECHNICAL FIELD

The present disclosure pertains to ultrasound systems and methods for identifying anatomical features in ultrasound images using a neural network. Particular implementations involve systems configured to generate an adaptive scanning protocol based on the anatomical features and conditions identified by a neural network.

BACKGROUND

Ultrasonography is widely used for evaluating prenatal growth and development. Ultrasound scans are performed throughout the pregnancy to assess viability, anatomy, age, and pre-delivery status. For high-risk pregnancies, weekly or biweekly scans may be needed. Typical evaluations may involve imaging a pre-specified list of anatomical features, often in a particular sequence, to collect measurements indicative of fetal age and health. For example, femur length, abdominal circumference, and head circumference are often measured.

Even routine scans require collection of a large number of images and measurements that can be overwhelming to users, especially those having little experience. The long list of necessary measurements may also be different at different pregnancy stages, further increasing the difficulty of acquiring accurate measurements. Existing workflow solutions designed to provide an ordered scan protocol are inflexible and often require users to measure specific features in a specific order. New technologies configured to reduce the difficulty associated with performing prenatal ultrasound scans, especially for novice users, are thus desired.

SUMMARY

The present disclosure describes systems and methods for performing ultrasonic evaluations of various anatomical objects. While examples herein specifically address prenatal evaluations of a fetus, it should be understood to those skilled in the art that the disclosed systems and methods are described with respect to fetal assessment for illustrative purposes only, and that anatomical assessments can be performed at a range of timepoints on a variety of objects within a patient, including but not limited to the heart and the lungs, for example. In some embodiments, the system may be configured to improve the accuracy, efficiency and automation of prenatal ultrasound scans, or ultrasound scanning protocols associated with other clinical applications (e.g., cardiac, liver, breast, etc.), for example by identifying specific anatomical features, movement of anatomical features or structures (e.g., fetal movements) and positioning of said anatomical features or structures, and in response to such determinations, adaptively guiding a user through an ultrasound scan, such as a fetal scan, in compliance with established medical guidelines. Some embodiments involve standard view classification performed by a neural network uniquely configured to classify anatomical features of the tissue, organ, or bodily structure in real time as ultrasound images of the tissue, organ, or bodily structure are acquired.

Some specific embodiments may include computational modules configured to detect fetal activity or movement and a current fetal position. Each of the determinations made by the neural network and the activity/positioning modules can be fed into a second neural network configured to, based on the received inputs, recommend a next fetal measurement to be acquired and/or anatomical feature to be imaged. In some embodiments, systems may also be configured to detect fetal abnormalities, and in response to detecting such abnormalities, recommend additional measurements to further interrogate the abnormalities. Systems can also include a user interface configured to display a worklist of required measurements and/or imaging views of a fetus. The user interface can be configured to indicate which images and measurements have been completed and which images and measurements still need to be acquired in automated fashion or responsive to user input. Systems in accordance with the principles of the present invention may increase the efficiency of prenatal assessment by facilitating user decision-making and anatomical interpretation required during a prenatal ultrasound scan.

In accordance with some examples, an ultrasound imaging system may include an ultrasound transducer configured to acquire echo signals responsive to ultrasound pulses transmitted toward a target region and one or more processors in communication with the ultrasound transducer. The processors may be configured to generate at least one image frame from the ultrasound echoes and provide the image frame to a first neural network, the first neural network configured to identify an anatomical feature of an object in the image frame. The processors may also be configured to provide an indication of the anatomical feature to a second neural network, the second neural network configured to determine an anatomical measurement to be obtained based, in part, on the anatomical feature identified by the first neural network in accordance with a list of required measurements. The processors can also cause an indicator of the anatomical measurement to be obtained to be displayed on a user interface in communication with the processors.

In some examples, the processors may be further configured to generate an instruction for adjusting the ultrasound transducer based on the anatomical measurement to be obtained. In some embodiments, the processors can be further configured to identify a movement of the object and a current position of the object. In some examples, the processors may be further configured to provide an indication of the movement and current position of the object to the second neural network which is configured to determine the anatomical measurement to be obtained based in part on the movement and current position of the object. In some embodiments, the processors may be configured to identify a movement of the object by cross-correlating a subset of lines of consecutive image frames generated from the ultrasound echoes. In some examples, the processors may be configured to identify a current position of the object by extracting anatomical features from the image frame and inputting the extracted anatomical features into a recurrent neural network. In some embodiments, the second neural network may be configured to implement a recommender system configured to associate the anatomical feature identified by the first neural network with an action for obtaining the anatomical measurement to be obtained. In some examples, the first neural network can be operatively associated with a training algorithm configured to receive an array of training inputs and known outputs, where the training inputs comprise ultrasound image frames containing anatomical features of an object, and the known outputs comprise a view classification based on the anatomical features. In some examples, the user interface can be configured to display the list of required measurements. In some embodiments, the user interface may be configured to update the list of required measurements based in part on measurements that have been obtained by a user. In some examples, the anatomical measurement to be obtained may include a measurement obtainable by implementing a smallest possible adjustment of the ultrasound transducer. In some embodiments, the anatomical measurement to be obtained may include a measurement obtainable at or above an accuracy threshold.

In accordance with some examples, a method of ultrasound imaging may involve acquiring echo signals responsive to ultrasound pulses transmitted into a target region by a transducer operatively coupled to an ultrasound system, generating at least one image frame from the ultrasound echoes, and providing the image frame to a first neural network, the first neural network configured to identify an anatomical feature of an object in the image frame. In some examples, the method may also involve providing an indication of the anatomical feature to a second neural network. The second neural network can be configured to determine an anatomical measurement to be obtained based in part on the anatomical feature identified by the first neural network in accordance with a list of required measurements. The method may further involve causing an indicator of the anatomical measurement to be obtained to be displayed on a user interface in communication with the processors.

In some embodiments, the method may further involve generating an instruction for adjusting the ultrasound transducer based on the anatomical measurement to be obtained. In some examples, the method may also involve identifying a movement of the object and a current position of the object. In some embodiments, the method also involves providing an indication of the movement and current position of the object to the second neural network which determines the anatomical measurement to be obtained. Identifying the movement of the object may involve cross-correlating a subset of lines of consecutive image frames generated from the ultrasound echoes. Identifying the current position of the object may involve extracting anatomical features from the image frame and inputting the extracted anatomical features into a recurrent neural network. In some embodiments, the method also involves displaying and updating the list of requirement measurements based in part on measurements that have been obtained by a user.

The present disclosure describes systems and methods for performing prenatal evaluations of a fetus. Embodiments include systems configured to improve the accuracy, efficiency and automation of prenatal ultrasound scans by identifying specific anatomical features, fetal movement and positioning, and in response to such determinations, adaptively guiding a user through a fetal scan in compliance with established medical guidelines. Embodiments involve fetal view classification performed by a neural network uniquely configured to classify anatomical features of a fetus in real time as ultrasound images of the fetus are acquired. Embodiments may also include computational modules configured to detect fetal activity or movement and a current fetal position. Each of the determinations made by the neural network and the activity/positioning modules can be fed into a second neural network configured to, based on the received inputs, recommend a next fetal measurement to be acquired and/or anatomical feature to be imaged. In some embodiments, systems may also be configured to detect fetal abnormalities, and in response to detecting such abnormalities, recommend additional measurements to further interrogate the abnormalities. Systems can also include a user interface configured to display a worklist of required measurements and/or imaging views of a fetus. The user interface can be configured to indicate which images and measurements have been completed and which images and measurements still need to be acquired in automated fashion or responsive to user input. The systems described herein can increase the efficiency of prenatal assessment by facilitating user decision-making and anatomical interpretation required during a prenatal ultrasound scan.

In accordance with some examples, an ultrasound imaging system may include an ultrasound transducer configured to acquire echo signals responsive to ultrasound pulses transmitted toward a target region and one or more processors in communication with the ultrasound transducer. The processors may be configured to generate at least one image frame from the ultrasound echoes and apply a first neural network to the image frame, the first neural network configured to identify an anatomical feature of a fetus in the image frame. The processors may be further configured to apply a second neural network to the anatomical feature identified by the first neural network, the second neural network configured to determine an anatomical measurement to be obtained based, in part, on the anatomical feature identified by the first neural network in accordance with a list of required measurements. The processors may be further configured to cause an indicator of the anatomical measurement to be obtained to be displayed on a user interface in communication with the processors.

In some examples, the processors are further configured to generate an instruction for adjusting the ultrasound transducer based on the anatomical measurement to be obtained. In some embodiments, the processors are further configured to identify a movement of the fetus and a current position of the fetus. In some examples, the processors are further configured to apply the second neural network to the movement and current position of the fetus such that the second neural network is configured to determine the anatomical measurement to be obtained based in part on the movement and current position of the fetus. In some embodiments, the processors are configured to identify a movement of the fetus by cross-correlating a subset of lines of consecutive image frames generated from the ultrasound echoes. In some examples, the processors are configured to identify a current position of the fetus by extracting anatomical features from the image frame and inputting the extracted anatomical features into a recurrent neural network. In some embodiments, the second neural network is configured to implement a recommender system configured to associate the anatomical feature identified by the first neural network with an action for obtaining the anatomical measurement to be obtained. In some examples, the first neural network is operatively associated with a training algorithm configured to receive an array of training inputs and known outputs, wherein the training inputs comprise ultrasound image frames containing anatomical features of a fetus, and the known outputs comprise a view classification based on the anatomical features. In some embodiments, the user interface is configured to display the list of required measurements. In some examples, the user interface is configured to update the list of required measurements based in part on measurements that have been obtained by a user. In some embodiments, the anatomical measurement to be obtained comprises a measurement obtainable by implementing a smallest possible adjustment of the ultrasound transducer. In some embodiments, the anatomical measurement to be obtained comprises a measurement obtainable at or above an accuracy threshold.

In accordance with some examples, a method of ultrasound imaging may involve acquiring echo signals responsive to ultrasound pulses transmitted into a target region by a transducer operatively coupled to an ultrasound system, generating at least one image frame from the ultrasound echoes, and applying a first neural network to the image frame, the first neural network configured to identify an anatomical feature of a fetus in the image frame. A method may also involve applying a second neural network to the anatomical feature identified by the first neural network, the second neural network configured to determine an anatomical measurement to be obtained based in part on the anatomical feature identified by the first neural network in accordance with a list of required measurements. The method may also involve causing an indicator of the anatomical measurement to be obtained to be displayed on a user interface in communication with the processors.

In some embodiments, the method may further involve generating an instruction for adjusting the ultrasound transducer based on the anatomical measurement to be obtained. In some examples, the method further involves identifying a movement of the fetus and a current position of the fetus. In some embodiments, the method also involves applying the second neural network to the movement and current position of the fetus to determine the anatomical measurement to be obtained. In some examples, identifying the movement of the fetus comprises cross-correlating a subset of lines of consecutive image frames generated from the ultrasound echoes. In some embodiments, identifying the current position of the fetus comprises extracting anatomical features from the image frame and inputting the extracted anatomical features into a recurrent neural network. In some examples, the method may further involve displaying and updating the list of requirement measurements based in part on measurements that have been obtained by a user.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

Figure 1:
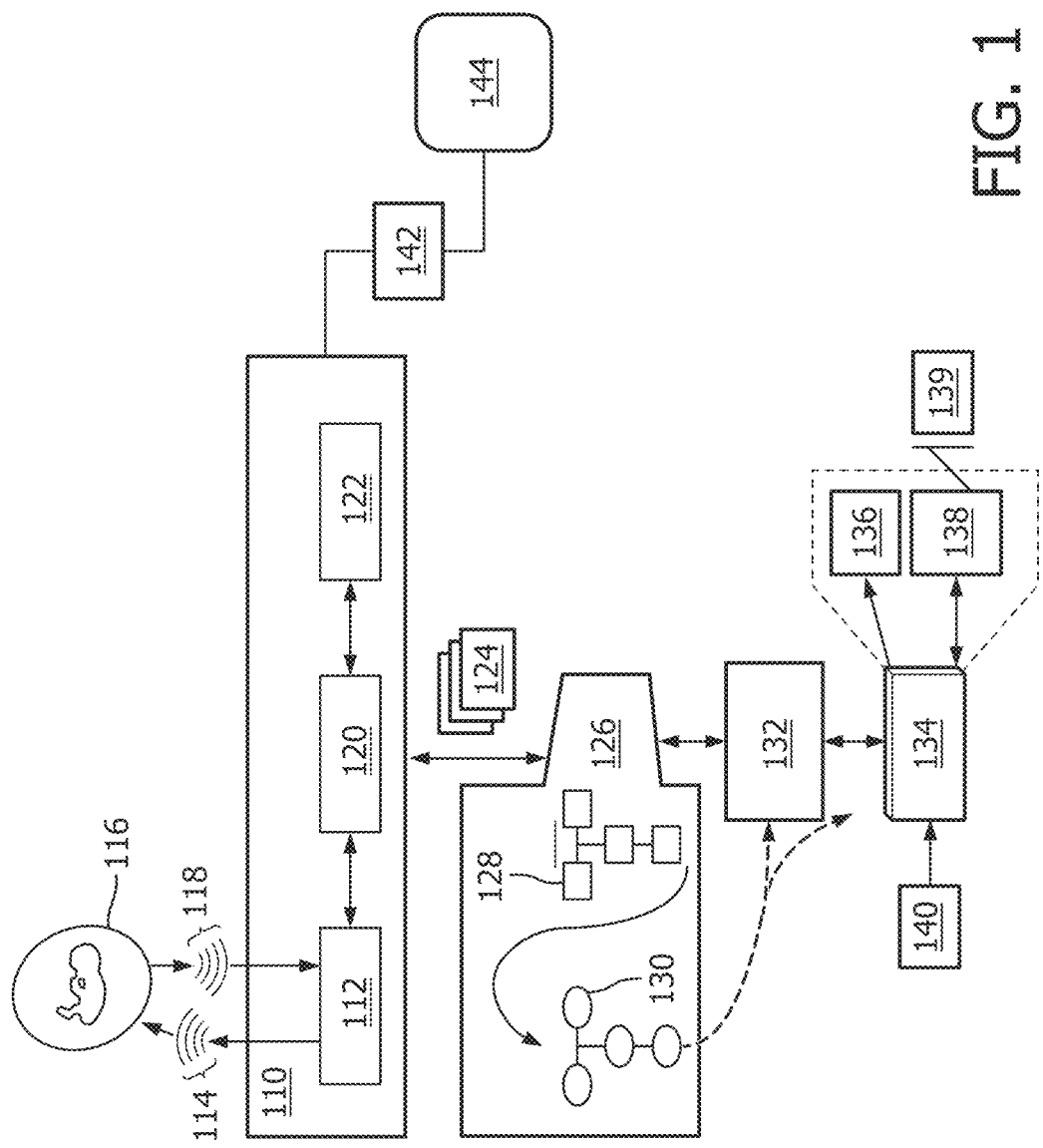
FIG. 1 is a block diagram of an ultrasound system in accordance with principles of the present inventions.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

An ultrasound system according to the present disclosure may implement one or more neural networks, for example at least one deep neural network (DNN), convolutional neural network (CNN) or the like, which is uniquely synced with data acquisition hardware and a user interface. Example systems may utilize a neural network to identify various features of a developing fetus, e.g., a femur, detected via ultrasound imaging, and classify a current image view based on the features detected. Systems may also utilize a neural network to generate and update a prenatal assessment protocol that is adaptive to the various anatomical features identified, along with a current position of the fetus and any movement thereof. In various examples, the neural network(s) may be trained using any of a variety of currently known or later developed machine learning techniques to obtain a neural network (e.g., a machine-trained algorithm or hardware-based system of nodes) that is configured to analyze input data in the form of ultrasound image frames and identify certain features, including the presence and in some embodiments, the size, of one or more prenatal anatomical features. Neural networks implemented herein may also be configured to analyze input data in the form of the identified anatomical features, anatomical measurements, binary movement classifications and/or fetal position determinations, and based on this input, determine a next step in an adaptive scan protocol. Neural networks may provide an advantage over traditional forms of computer programming algorithms in that they can be generalized and trained to recognize data set features by analyzing data set samples rather than by reliance on specialized computer code. By presenting appropriate input and output data to a neural network training algorithm, neural network(s) of an ultrasound system according to the present disclosure can be trained to identify a plurality of anatomical features and/or guide a user through an ultrasound scan of a fetus based in part on the anatomical features identified. Movement detection performed by systems herein can further inform the adaptive scanning protocol elucidated by a neural network, such that fetal movement can also influence a particular scan.

An ultrasound system in accordance with principles of the present invention may include or be operatively coupled to an ultrasound transducer configured to transmit ultrasound pulses toward a medium, e.g., a human body or specific portions thereof, and generate echo signals responsive to the ultrasound pulses. The ultrasound system may include a beamformer configured to perform transmit and/or receive beamforming, and a display configured to display, in some examples, ultrasound images generated by the ultrasound imaging system. The ultrasound imaging system may include one or more processors and at least one neural network, which may be implemented in hardware and/or software components. The neural network can be machine-trained to identify one or more bodily features, such as various bones, organs and/or cavities, and output an indication of the presence and/or absence thereof, along with any measurements of such features obtained via ultrasound imaging.

The neural networks utilized according to the present disclosure may be hardware—(e.g., neurons are represented by physical components) or software-based (e.g., neurons and pathways implemented in a software application), and can use a variety of topologies and learning algorithms for training the neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a machine-trained algorithm for identifying various anatomical features of a fetus within ultrasound images and, in some examples, output an indication of the presence or absence of such features. The ultrasound system may include a display or graphics processor, which is operable to arrange the ultrasound image and/or additional graphical information, which may include a worklist of features to be imaged and/or measured, annotations, tissue information, patient information, indicators, and other graphical components, in a display window for display on a user interface of the ultrasound system. In some embodiments, the ultrasound images and tissue information, including information regarding the presence, absence and/or identity of prenatal anatomical features, may be provided to a storage and/or memory device, such as a picture archiving and communication system (PACS) for reporting purposes, developmental progress tracking, or future machine training (e.g., to continue to enhance the performance of the neural network). In some examples, ultrasound images obtained during a scan may be selectively or automatically transmitted, e.g., over a communications network, to a specialist trained to interpret the information embodied in the images, e.g., an obstetrician-gynecologist, an ultrasound specialist, a physician, or other clinician, thereby allowing a user to perform the ultrasound scans necessary for fetal monitoring and/or diagnosis in various locations. The user operating the ultrasound imaging system and the specialist may be located in separate locations during an ultrasound scan, such that transmission of the ultrasound images and/or the information gleaned therefrom may occur over a geographical distance.

Figure 2:
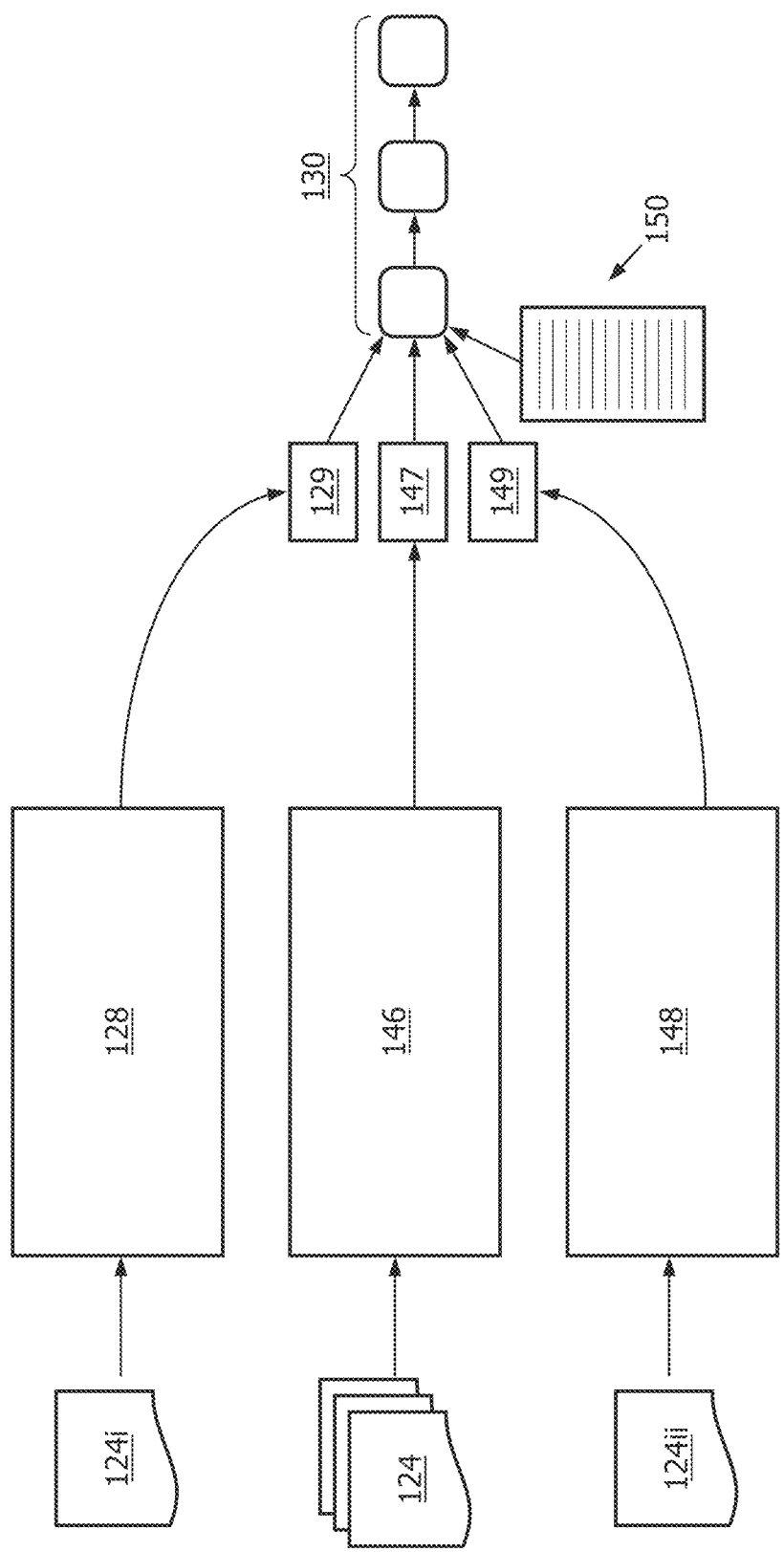
FIG. 2 is a block diagram of an operational arrangement of system components implemented in accordance with principles of the present inventions.

FIG. 1 shows an example ultrasound system 100 according to principles of the present disclosure. The ultrasound system 100 may include an ultrasound data acquisition unit 110. The ultrasound data acquisition unit 110 can include an ultrasound probe which includes an ultrasound sensor array 112 configured to transmit ultrasound pulses 114 into a region 116 of a subject, e.g., abdomen, and receive ultrasound echoes 118 responsive to the transmitted pulses. The region 116 may include a developing fetus, as shown, or a variety of other anatomical objects, such as the heart or the lungs. As further shown, the ultrasound data acquisition unit 110 can include a beamformer 120 and a signal processor 122, which can be configured to generate a stream of discrete ultrasound image frames 124 from the ultrasound echoes 118 received at the array 112. The system can also include a data processor 126, e.g., a computational module or circuitry, configured to implement a first neural network 128. The first neural network 128 can be configured to receive the image frames 124, either directly from the signal processor 122 or via the data processor 126, determine a presence, absence and/or identity of at least one anatomical feature within each frame, and classify an image view, e.g., a current image view, based on this determination. The data processor 126 may also be configured to implement a second neural network 130, which can be configured to receive and process the view classification output generated by the first neural network 128. Specific outputs received by the second neural network 130 can include, in addition to the view/feature classifications generated by the first neural network 128, indications of fetal movement, relative fetal position information, and/or a stored list of required anatomical features and specific measurements thereof to be obtained during a fetal scan. These outputs can be input to the second neural network 130 from one or more processing modules, which may be included within data processor 126 (FIG. 2). In some examples, the system 100 also includes a display processor 132 coupled with the data processor and a user interface 134. The display processor 132 can link the neural networks 128, 130 to the user interface 134, enabling the neural network outputs to be displayed on or modify the information displayed on the user interface. In various embodiments, the user interface 134 may receive the outputs directly from the second neural network 130, or after additional processing via the data processor 132. In some examples, the display processor 132 may be configured to generate ultrasound images 136 from the image frames 124, received either directly or indirectly from the data acquisition unit 110, and generate an adaptive scan protocol 138 that can include a worklist updated to reflect the images and/or measurements obtained and the images and/or measurements that have yet to be obtained. In some examples, the scan protocol 138 may convey the presence of an anatomical feature within a current image frame 124, and in some embodiments, whether the image of such feature is sufficient to accurately measure the feature or whether additional images of the feature are needed. The user interface 134 can be configured to display the ultrasound images 136 of the region 116 in real time as an ultrasound scan is being performed, along with the adaptive scan protocol 138. The user interface 134 may also be configured to receive a user input 140 at any time before, during, or after an ultrasound scan. For example, the user interface 134 may be interactive, receiving user input 140 indicating confirmation that an anatomical feature has been assessed, and adapting a display responsive to the input. As further shown, the scan protocol 138 may also be input into the user interface 134. The configuration of the system 100 shown in FIG. 1 may vary. For example, the system 100 can be portable or stationary. Various portable devices, e.g., laptops, tablets, smart phones, or the like, may be used to implement one or more functions of the system 100. In examples that incorporate such devices, the ultrasound sensor array 112 may be connectable via a USB interface, for example. In some examples, various components shown in FIG. 1 may be combined. For instance, the first neural network 128 and second neural network 130 may be merged into a single neural network. According to such embodiments, the output generated by the first neural network 128 may still be input into the second neural network 130, but the two networks may constitute sub-components of a larger, layered network, for example.

The ultrasound data acquisition unit 110 can be configured to acquire ultrasound data from one or more regions of interest 116, which may include a fetus and features thereof. The ultrasound sensor array 112 may include at least one transducer array configured to transmit and receive ultrasonic energy. The settings of the ultrasound sensor array 112 can be preset for performing a prenatal scan of a fetus, and in embodiments, can be readily adjustable during a particular scan in response to movement of the fetus or detection of one or more features. A variety of transducer arrays may be used, e.g., linear arrays, convex arrays, or phased arrays. The number and arrangement of transducer elements included in the sensor array 112 may vary in different examples. For instance, the ultrasound sensor array 112 may include a 1D or 2D array of transducer elements, corresponding to linear array and matrix array probes, respectively. The 2D matrix arrays may be configured to scan electronically in both the elevational and azimuth dimensions (via phased array beamforming) for 2D or 3D imaging. In addition to B-mode imaging, imaging modalities implemented according to the disclosures herein can also include shear-wave and/or Doppler, for example.

A variety of users may handle and operate the ultrasound data acquisition unit 110 to perform the methods described herein. In some examples, the user may be an inexperienced, novice ultrasound operator unable to efficiently identify each anatomical feature of a fetus required in a given scan. Users of preexisting systems may typically need to follow an established protocol in a pre-specified order, for example assessing the fetal head/brain, then the femur, and then fetal facial structures. While experienced users may deviate from the sequence of assessments established by such protocols, deviation may require the users to maintain a mental list of complete and incomplete tasks. The systems herein overcome this problem by employing an imaging system coupled with deep learning and an intuitive user interface configured to provide an adaptive scan protocol that is responsive to image data acquired during a scan and the movement and current position of the fetus being evaluated. With reference to FIG. 1, the system 100 enables users to perform effective prenatal assessments by identifying anatomical features within acquired ultrasound image frames 124 and providing instructions to the users for acquiring image data for the next required anatomical feature specified in a worklist, which may be updated and displayed on the user interface 134. Because the system 100 is responsive to the anatomical features detected in a current image view and any current movement and/or position of the fetus, the user can be prompted to obtain images of certain features and, in some examples, required measurements of such features, in a manner that is adaptive to the physical status of the fetus with respect to the position and angular orientation of the data acquisition unit 110. In examples where a mechanical adjustment mechanism 142, e.g., a robotic arm, is used to control the position and/or orientation of the data acquisition unit 110, the instructions for acquiring image data may be communicated to a controller 144 configured to cause the adjustment mechanism to make the necessary adjustments automatically, without user input. The controller 144 may be configured to adjust the position, orientation and/or operational settings of the data acquisition unit 110 as part of an automatic feedback loop with the data processor 126. In some examples, the controller 144 can receive information regarding a current position of the ultrasound sensor array 112 and a direction the array needs to move or turn, which may be based at least in part on information received from the first neural network 128 and/or second neural network 130, along with information regarding a current fetal position (FIG. 2). The controller 144 can be equipped with one or more safety features, e.g., a force sensor configured to prevent the adjustment mechanism 142 from applying excess force to the fetal region 116. In some examples, the controller 144 is configured to receive user input 140, e.g., via the user interface 134, regarding the position of the transducer array 112 necessary to capture a next required measurement and/or image. By identifying anatomical features and providing precise instructions for proceeding through a prenatal scan, the systems disclosed herein may lead to more accurate and more efficient prenatal assessment.

The data acquisition unit 110 may also include a beamformer 120, e.g., comprising a microbeamformer or a combination of a microbeamformer and a main beamformer, coupled to the ultrasound sensor array 112. The beamformer 120 may control the transmission of ultrasonic energy, for example by forming ultrasonic pulses into focused beams. The beamformer 120 may also be configured to control the reception of ultrasound signals such that discernable image data may be produced and processed with the aid of other system components. The role of the beamformer 120 may vary in different ultrasound probe varieties. In some embodiments, the beamformer 120 may comprise two separate beamformers: a transmit beamformer configured to receive and process pulsed sequences of ultrasonic energy for transmission into a subject, and a separate receive beamformer configured to amplify, delay and/or sum received ultrasound echo signals. In some embodiments, the beamformer 120 may include a microbeamformer operating on groups of sensor elements for bother transmit and receive beamforming, coupled to a main beamformer which operates on the group inputs and outputs for both transmit and receive beamforming, respectively.

The signal processor 122 may be communicatively, operatively and/or physically coupled with the sensor array 112 and/or the beamformer 120. In the example shown in FIG. 1, the signal processor 122 is included as an integral component of the data acquisition unit 110, but in other examples, the signal processor 122 may be a separate component. In some examples, the signal processor may be housed together with the sensor array 112 or it may be physically separate from by communicatively (e.g., via a wired or wireless connection) coupled thereto. The signal processor 122 may be configured to receive unfiltered and disorganized ultrasound data embodying the ultrasound echoes 118 received at the sensor array 112. From this data, the signal processor 122 may continuously generate a plurality of ultrasound image frames 124 as a user scans the fetal region 116.

The data processor 126 can be configured to perform multiple functions. As mentioned above, the data processor 126 can be configured to implement a neural network 128, which can be configured to classify images into distinct categories, for example "full view," "head," "abdominal," "chest," or "extremities." Sub-categories can include, for example, "stomach," "bowel," "umbilical cord," "kidney," "bladder," "legs," "arms," "hands," "femur," "spine," "heart," "lungs," "stomach," "bowel," "umbilical cord,"

"kidney," or "bladder." Classification results determined by the neural network 128 can be adaptive to a current ultrasound region of interest and/or the completed measurements within the prenatal assessment protocol. For example, if the region of interest is large and includes multiple sub-categories of anatomical features, such as the kidney, liver and umbilical cord, the neural network 128 may classify the current image as "abdominal," along with an indication of suggested features and/or measurements thereof to be obtained within the abdominal region.

Output generated by the neural network 128 can be input into a second neural network 130, which in some examples, comprises a convolutional neural network (CNN) configured to receive multiple input types. For example, input to the second neural network 130 can include the organ/view classification received from the first neural network 128, along with binary classifications of motion detection, approximated fetal position data, and/or a list of measurements to be obtained in accordance with a stored scan protocol. From these inputs, the second neural network 130 can determine and output a suggested next measurement to be obtained in accordance with the required measurements of a prenatal assessment protocol.

The system 100 may also include a display processor 132 coupled with the data processor 126 and the user interface 134. In various embodiments, the display processor 132 can be configured to generate ultrasound images 136 from the image frames 124 and an adaptive scan protocol 138 that includes a list of required fetal measurements, each of which may be accompanied by a status indicator showing whether or not each measurement has been obtained. The user interface 134 may be configured to display and update the adaptive scan protocol 138 in real time as an ultrasound scan is being performed. In some examples, the user interface 134 may be further configured to display instructions 139 for adjusting the data acquisition unit 110 in the manner necessary to obtain the next recommended measurements. The user input 140 received at the user interface 134 can be in the form of a manual confirmation that a particular measurement has been obtained. In some embodiments, the user input 140 may comprise agreement or disagreement with a next recommended measurement. In this manner, a user may override a recommended measurement. In some examples, the user input 140 can include instructions for implementing particular operational parameters necessary for imaging and/or measuring specific anatomical features, e.g., biparietal diameter, occipito-frontal diameter, head circumference, abdominal circumference, femur length, amniotic fluid index, etc. The operational parameters can include focal depths, pulse frequencies, scan line numbers, scan line densities, or other settings.

FIG. 2 is a block diagram of an example arrangement of computational modules and neural networks that can be implemented by the data processor 126. As shown, the first neural network 128 can be configured to classify anatomical features and/or views in each individual image frame 124*i* acquired by a data acquisition unit and input into the network. The neural network 128 generates classification outputs 129 embodying the specific sub-region and/or anatomical feature(s) included in each image frame 124*i*. A motion detection module 146 can be configured to cross-correlate the lines included in consecutive image frames 124 to detect movement of fetal tissue and/or bodily fluids, e.g., blood flow, generating a binary motion output 147. A position approximation module 148 can be configured to determine a current position of a fetus based on, for example, an overview image 124*ii* of the fetus being evaluated, and output a position indication 149. A stored list 150 of required anatomical features and specific measurements thereof can also be input into the second neural network 130, which the network may reference to determine a next best measurement to recommend to a user. The neural networks 128, 130 and modules 146, 148 can be implemented concurrently or successively.

The motion detection module 146 can be configured to cross-correlate consecutive image frames 124 by implementing one or more algorithms, such as a 2D cross-correlation algorithm. To reduce computational load and processing time, the module 146 may perform cross-correlation operations over a sub-portion of the image frames 124, e.g., a subset of image lines, instead of each image frame in its entirety. Motion detection performed by the module 146 can improve overall computational efficiency by eliminating fetal measurements that will certainly or likely fail, or be inaccurate, due to motion of the fetus. For example, blood flow and/or cardiac assessment should not be performed when significant motion is occurring, which the second neural network 130, operating in tandem with the motion detection module 146, can be configured to detect. In some examples, the motion detection module 146 may determine, alone or in conjunction with one or more additional processors, a confidence level associated with classifying and/or measuring an anatomical feature. A high confidence level can indicate that it is likely that a view classification determined by the first neural network 128 is correct. In some embodiments, the confidence level may be determined prior to implementation of the first neural network 128, such that a low confidence level indicates that it is unlikely an image classification determined by the first neural network 128 would be correct. According to such examples, a low confidence level may block implementation of the first neural network 128. In the event that the network is blocked, a user may override the low confidence level to proceed with image classification and/or implementation of the second neural network 130. Low confidence levels may be caused by fetal movement. Manual override capability may be necessary to proceed with a prenatal scan despite the occasionally unavoidable difficulty associated with imaging a fetus that exhibits nearly constant movement.

The position approximation module 148 can be configured to orient the system 100 to the current position of the fetus relative to the position of the data acquisition unit 110. For example, given the overview image 124*ii* acquired by a user screening through the region of interest 116, the fetal position and relative positions of the individual fetal body parts can be identified. Identifying the fetal position may be achieved by detecting one or more anatomical features and/or the spatial relationship between such features. In some examples, identifying the fetal position may be achieved via convolutional feature extraction. Extracted features may be input into a recurrent neural network, for example, which can be trained to determine a fetal position and/or orientation based on the features identified. The fetal part positions detected by the position approximation module 148 can be fed into the second neural network to inform the determination of a next-best fetal measurement. For example, if the fetus is lying sideways, it may be easier and/or more efficient to assess the relatively large fetal body parts, such as the head or abdominal circumferences, rather than smaller features, such as the nose, lips and genitals. Imaging and/or obtaining measurements of larger anatomical features may require the user to sweep the ultrasound transducer in a consistent orientation at the beginning of the scan, e.g., laterally from left to right.

The stored list 150 of required anatomical features can be obtained, in some embodiments, from the American Institute of Ultrasound in Medicine, although established protocols can also be obtained from other entities, e.g., The Society of Obstetricians and Gynecologists of Canada. In some examples, the list 150 can be customized to fit the needs of specific users or institutions. The second neural network 130 can be trained using the most comprehensive list of measurements to increase the robustness of the system 100. Anatomical features/measurements not of interest to a particular user can simply be removed from the list 150 referenced during a specific scan so that they will not be recommended by the system during the scan.

The second neural network 130 can be configured to provide suggestions for the next measurement that can or should be obtained. The network 130 can implement a recommender system, such as that shown in FIG. 4. The next measurement can be recommended based on one or more factors. For example, the next recommended measurement may be the measurement that is obtainable by implementing the smallest or most minor adjustments to the ultrasound transducer used to obtain the ultrasound images. The adjustments can including operating parameters, e.g., focal depth, or the position and/or orientation of the ultrasound transducer. By recommending measurements in this manner, a user may quickly and efficiently progress through a scan by minimizing the extent of imaging adjustments required to obtain successive measurements. In addition or alternatively, the next recommended measurement can be the measurement that is obtainable at or above an accuracy threshold. The accuracy threshold may establish the minimum level of image quality that is acceptable for imaging and/or measuring an anatomical feature of a fetus. For instance, systems herein may not recommend, in some examples, a blood flow measurement if fetal movement has been detected because such a measurement would be unreliable, falling below the acceptable accuracy threshold for measuring blood flow. In some embodiments, the threshold may be defined based on established guidelines.

Figure 3A:
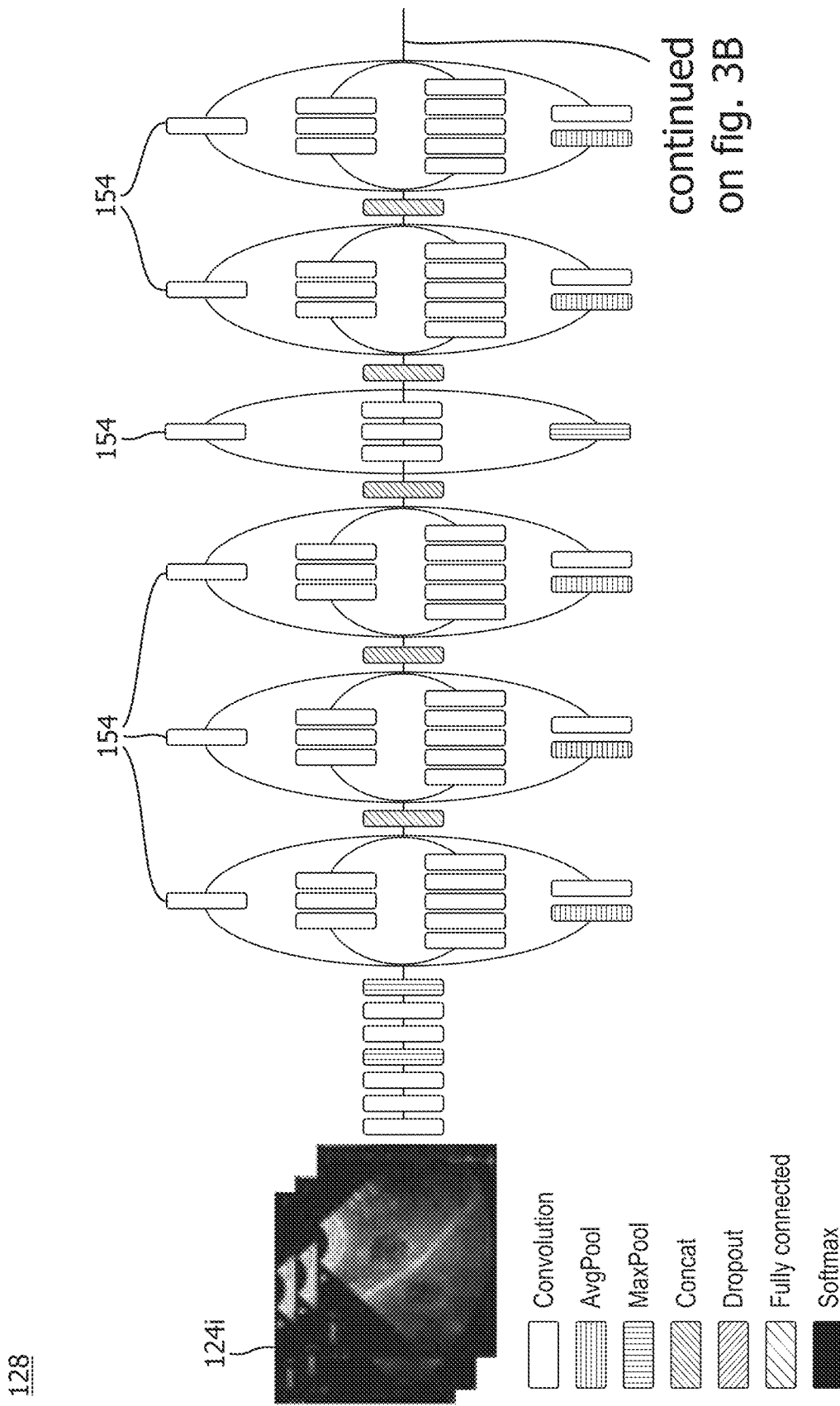
FIG. 3 is a block diagram of a neural network configured to classify fetal images in accordance with principles of the present inventions.
Figure 3B:
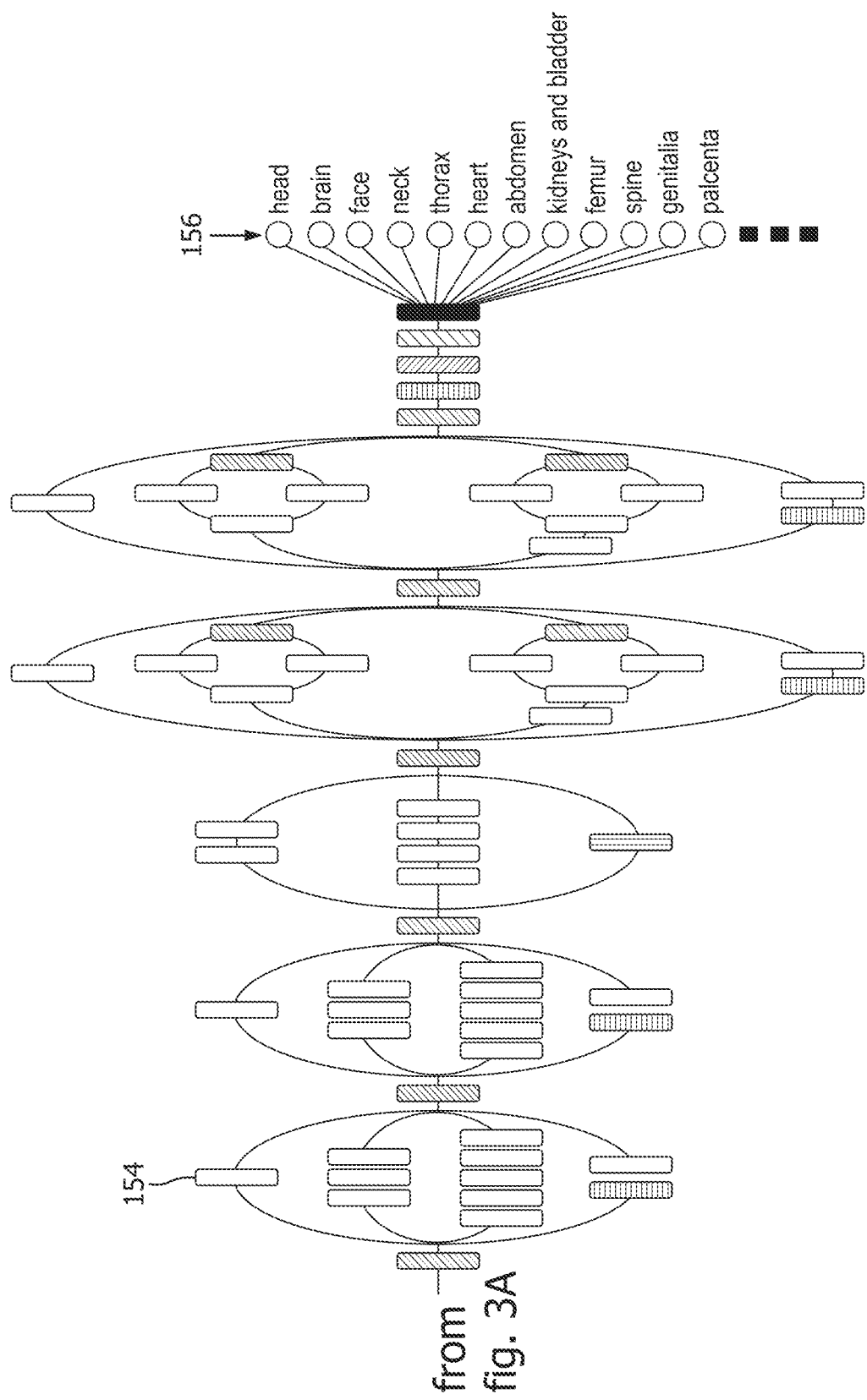

FIG. 3 is a block diagram of a neural network 128 configured to classify fetal images in accordance with principles of the present inventions. In the embodiment shown, the neural network 128 is a convolutional neural network (CNN). The network architecture shown in FIG. 3, which is customized for detecting the presence and type of anatomical features in image data, represents only one example of the arrangement of neural layers and sub-layers, as well as the connectivity therebetween, which may be implemented according to examples of the present invention. For example, the number of layers 154 may be greater for a neural network configured to identify more anatomical features. In various examples, the network architecture shown in FIG. 3 can be modified by adjusting the weights and dense layers to output a multi-label classifier with a length equal to the number of different anatomical features. As explained above and shown again in FIG. 3, the neural network 128 can be trained to receive an input in the form of ultrasound image frames 124, which may each contain zero, one, or multiple anatomical features of one or more fetuses.

The neural network 128 can be built using transfer learning in some embodiments. In specific examples, existing neural network models, e.g., Inception v4, can be modified to perform fetal view classification in accordance with the present disclosure. According to such examples, the network 128 can be trained with a large clinical database of ultrasound images obtained during prenatal ultrasound scans, the images collectively including a diverse variety of anatomical features. The final layer 156 may be configured to determine the specific features present within an image and, in embodiments, classify an image view based on the feature(s) identified. The neural network 128 can then generate an output conveying the presence, absence and/or identity of the features and/or view classification identified. For this reason, the final layer 156 may be referred to as the "output layer." In some examples, the neural network 128 can be configured to determine whether an abnormality is present in an image frame. Abnormality detection may involve comparing a measurement of an anatomical feature to a stored range of common measurements of the same anatomical feature, the stored range based on a large sample size of images. Observed measurements falling outside the common range of measurements can be flagged as a potential abnormality.

The neural network 128 may be implemented, at least in part, in a computer-readable medium comprising executable instructions, which when executed by a processor, e.g., data processor 126, may cause the processor to perform a machine-trained algorithm to determine the presence, absence and/or type of anatomical features contained in an image frame based on the acquired echo signals embodied therein. To train the neural network 128, training sets which include multiple instances of input arrays and output classifications may be presented to the training algorithm(s) of the neural network 128 (e.g., AlexNet training algorithm, as described by Krizhevsky, A., Sutskever, I. and Hinton, G. E. "*ImageNet Classification with Deep Convolutional Neural Networks*," NIPS 2012 or its descendants).

A neural network training algorithm associated with the neural network 128 can be presented with thousands or even millions of training data sets in order to train the neural network to identify anatomical features and characterize a current image view based on the presence of the features identified. In various examples, the number of ultrasound images used to train the neural network 128 may range from about 50,000 to 200,000 or more. The number of images used to train the network may be increased if higher numbers of different anatomical features are to be identified. The number of training images may differ for different anatomical features, and may depend on variability in the appearance of certain features. For example, certain features may appear more consistently at certain stages of prenatal development than other features. Training the network 128 to identify features with moderate to high variability may require more training images. In some embodiments, the training may be supervised. For instance, the final output of the neural network 128, which may include at least one anatomical feature or view classification, may be either confirmed or rejected by an expert in ultrasound image interpretation.

Figure 4:
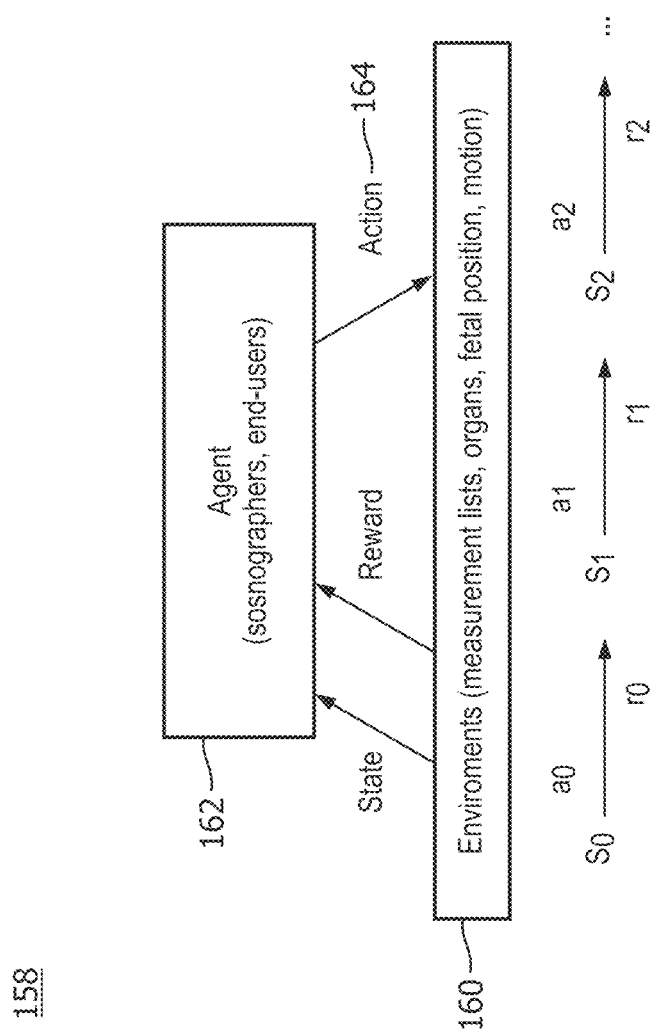
FIG. 4 is a block diagram of a recommender system configured to generate suggested next measurements in an adaptive scan protocol.

FIG. 4 is a block diagram of a recommender system 158 implemented by the second neural network 130. In the example shown, the recommender system 158 comprises a deep learning model configured to provide user suggestions for a next image and/or measurement to be obtained according to the adaptive protocol. As shown, input 160 in the form of measurement lists, organs, view classifications, fetal positions and/or combinations thereof, can be communicated to an agent 162, e.g., a sonographer, OBGYN or other end user, who may then recommend a certain action 164, e.g., a next measurement and any ultrasound probe adjustments necessary to obtained the measurement, based on the received input 160. Over time, the recommender system 158 can learn to associate certain inputs with specific recommended actions, such that the system can automatically recommend certain actions to be taken in response to input data received during a scan. For example, in response to obtaining input 160 that a current image view depicts an abdomen, the system 158 can be configured to recommend that the stomach be imaged and/or measured next, followed by the bowel and/or umbilical cord. In this manner, the next recommended images and/or measurements are based, at least in part, on the current field of view, such that a user can proceed through a scan in an intuitive, efficient fashion that may deviate from a sequential, pre-specified list of anatomical features to be assessed. The recommender system 158 can be trained over time based on feedback provided by a user. For instance, an action recommended by the recommender system 158 in response to an input can be reinforced when the user agrees with or confirms the action recommended by the system. Likewise, an action recommended by the recommender system 158 can be quashed when the user disagrees with or rejects the action recommended by the system, thereby teaching the system not to recommend the rejected action in response to the same or similar inputs in the future.

Figure 5:
FIG. 5 is an example user interface configured to guide a user through an adaptive scan protocol in accordance with principles of the present inventions.

FIG. 5 is an example user interface 500 configured to guide a user through an adaptive scan protocol in accordance with principles of the present inventions. As shown, a live ultrasound image 502 may be displayed concurrently with a current view description 504, a motion indicator 506, and a suggested next measurement indicator 508. In addition, a worklist 510 of anatomical features can be displayed. In some examples, a list of measurements 512 and calculations 514 may also be displayed. The current ultrasound imaging parameters 516 are also shown. The selection and arrangement of items displayed on the user interface 500 can vary in embodiments.

The user interface 500 can display the results of image classification and suggested actions determined by systems described herein. The user interface 500 can also be configured to update the worklist 510 of required measurements. In some examples, one or more indicators displayed on the user interface 500 can be color-coded to notify a user and for progress tracking. For example, completed measurements can be colored green in the worklist 510, while the next recommended measurements can be colored red, and the current measurement colored blue. In some embodiments, a confidence level associated with a current image view classification and/or the suggested next measurement may also be displayed, for example as a component of the current view description 504.

In the snapshot shown, a "full-view" of the fetus is displayed in the ultrasound image 502. At least some movement of the fetus is occurring, according to the "motion detected" status of the motion indicator 506. Based on the current view, the fact that the fetus is moving, and the previously obtained images/measurements, measuring the head and/or abdominal region is recommended as a next best step, according to indicator 508.

In additional examples, the user interface 500 may be further configured to guide or assist a user through a prenatal scan in accordance with the adaptive protocol generated by systems herein. The guidance can be generated by the second neural network 130 in the form of one or more instructions 518 for adjusting an ultrasound transducer in a manner necessary to obtain the next recommended image and/or measurement. For instance, if the head of a fetus has been most recently measured, the next recommended measurement may be of the abdominal region. To comply with this recommendation, the user interface 500 may display instructions 518 for adjusting an ultrasound transducer in a manner that enables images of the abdominal region to be obtained. Instructions may include directional commands, e.g., "Move ultrasound probe laterally," and/or technique-based commands, e.g., "Move ultrasound probe slower"; "Slow down"; "Stop"; "or "Continue." In some embodiments, the instructions may comprise modifications of one or more image acquisition parameters. For example, the user interface 500 may provide instructions 518 to alter the imaging plane, the focal depth and/or the pulse frequency of the transducer. In the event that an abnormality is detected, the user interface 500 may provide an instruction to hold the transducer steady at one location, thereby allowing further analysis. Slight adjustments in the imaging angle may also be recommended to more thoroughly characterize a detected abnormality.

Figure 6:
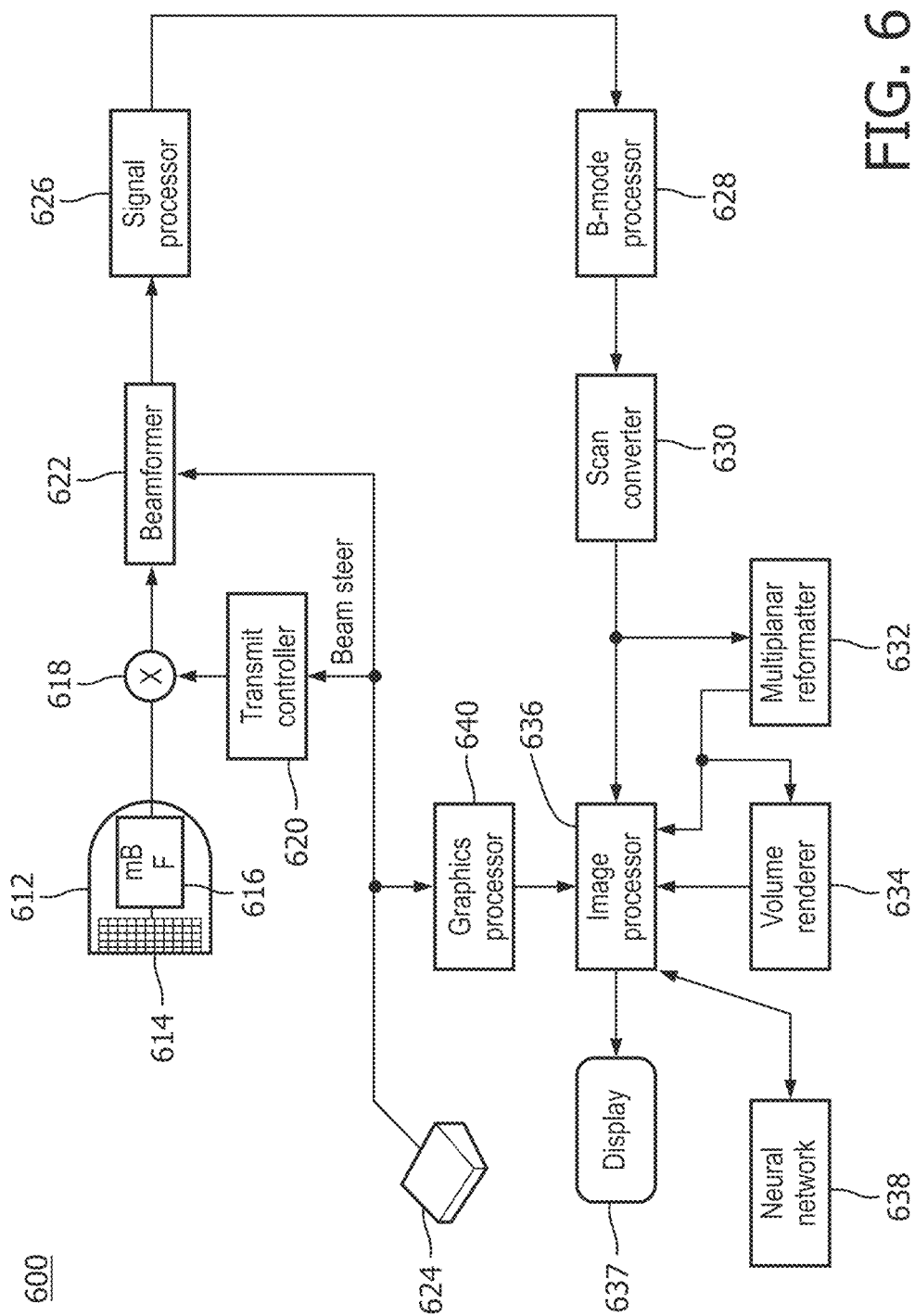
FIG. 6 is a block diagram of another ultrasound system in accordance with principles of the present inventions.

FIG. 6 is a block diagram of another ultrasound system 600 in accordance with principles of the present inventions. One or more components shown in FIG. 6 may be included within a system configured to generate an adaptive scan protocol for prenatal assessment. For example, any of the above-described functions of the signal processor 122 may be implemented and/or controlled by one or more of the processing components shown in FIG. 6, including for example, signal processor 626, B-mode processor 628, scan converter 630, multiplanar reformatter 632, volume renderer 634 and/or image processor 636.

In the ultrasonic imaging system of FIG. 6, an ultrasound probe 612 includes a transducer array 614 for transmitting ultrasonic waves into a region containing a fetus and receiving echo information responsive to the transmitted waves. In various embodiments, the transducer array 614 may be a matrix array or a one-dimensional linear array. The transducer array may be coupled to a microbeamformer 616 in the probe 612 which may control the transmission and reception of signals by the transducer elements in the array. In the example shown, the microbeamformer 616 is coupled by the probe cable to a transmit/receive (T/R) switch 618, which switches between transmission and reception and protects the main beamformer 622 from high energy transmit signals. In some embodiments, the T/R switch 618 and other elements in the system can be included in the transducer probe rather than in a separate ultrasound system component. The transmission of ultrasonic beams from the transducer array 614 under control of the microbeamformer 616 may be directed by the transmit controller 620 coupled to the T/R switch 618 and the beamformer 622, which receives input, e.g., from the user's operation of the user interface or control panel 624. A function that may be controlled by the transmit controller 620 is the direction in which beams are steered. Beams may be steered straight ahead from (orthogonal to) the transducer array, or at different angles for a wider field of view. The partially beamformed signals produced by the microbeamformer 616 are coupled to a main beamformer 622 where partially beamformed signals from individual patches of transducer elements are combined into a fully beamformed signal.

The beamformed signals may be communicated to a signal processor 626. The signal processor 626 may process the received echo signals in various ways, such as bandpass filtering, decimation, I and Q component separation, and/or harmonic signal separation. The signal processor 626 may also perform additional signal enhancement via speckle reduction, signal compounding, and/or noise elimination. In some examples, data generated by the different processing techniques employed by the signal processor 626 may be used by a data processor and/or at least one neural network to identify one or more anatomical features and/or image views and recommend a next image and/or measurement to be obtained. The processed signals may be coupled to a B-mode processor 628, which may employ amplitude detection for imaging structures in the body. The signals produced by the B-mode processor 628 may be coupled to a scan converter 630 and a multiplanar reformatter 632. The scan converter 630 may arrange the echo signals in the spatial relationship from which they were received in a desired image format. For instance, the scan converter 630 may arrange the echo signals into a two dimensional (2D) sector-shaped format. The multiplanar reformatter 632 may convert echoes which are received from points in a common plane in a volumetric region of the body into an ultrasonic image of that plane, as described in U.S. Pat. No. 6,443,896 (Detmer). In some examples, a volume renderer 634 may convert the echo signals of a 3D data set into a projected 3D image as viewed from a given reference point, e.g., as described in U.S. Pat. No. 6,530,885 (Entrekin et al.). The 2D or 3D images may be communicated from the scan converter 630, multiplanar reformatter 632, and volume renderer 634 to an image processor 636 for further enhancement, buffering and/or temporary storage for display on an image display 637. Prior to their display, a neural network 638 may be implemented to classify each image based on anatomical features identified therein. In embodiments, the neural network 638 may be implemented at various processing stages, e.g., prior to the processing performed by the image processor 636, volume renderer 634, multiplanar reformatter 632, and/or scan converter 630. In some examples, more than one neural network may be implemented, such that the neural network 638 shown in FIG. 6 represents two or more neural communicatively coupled networks. A graphics processor 640 can generate graphic overlays for display with the ultrasound images. These graphic overlays may contain, e.g., standard identifying information such as patient name, date and time of the image, imaging parameters, and the like, and also various outputs generated by the neural network 638, such as one or more indicators conveying the presence, absence and/or identity of one or more anatomical features embodied in a current image and/or whether various anatomical features have been observed and/or measured and/or which anatomical features have yet to be observed and/or measured in accordance with a stored worklist. Graphic overlays may also include visual instructions, e.g., text and/or symbols, for guiding a user of the system 600 through an adaptive ultrasound scan in a manner necessary to obtain images and/or measurements required for a prenatal assessment. In some examples, the graphics processor may receive input from the user interface 624, such as a typed patient name or confirmation that an instruction displayed or emitted from the interface has been acknowledged and/or implemented by the user of the system 600. The user interface 624 may also receive input regarding the selection of particular imaging modalities and the operating parameters included in such modalities, input prompting adjustments to the settings and/or parameters used by the system 600, input requesting additional instructions or assistance for performing an ultrasound scan, and/or input requesting that one or more ultrasound images be saved and/or transmitted to a remote receiver. The user interface may also be coupled to the multiplanar reformatter 632 for selection and control of a display of multiple multiplanar reformatted (MPR) images.

Figure 7:
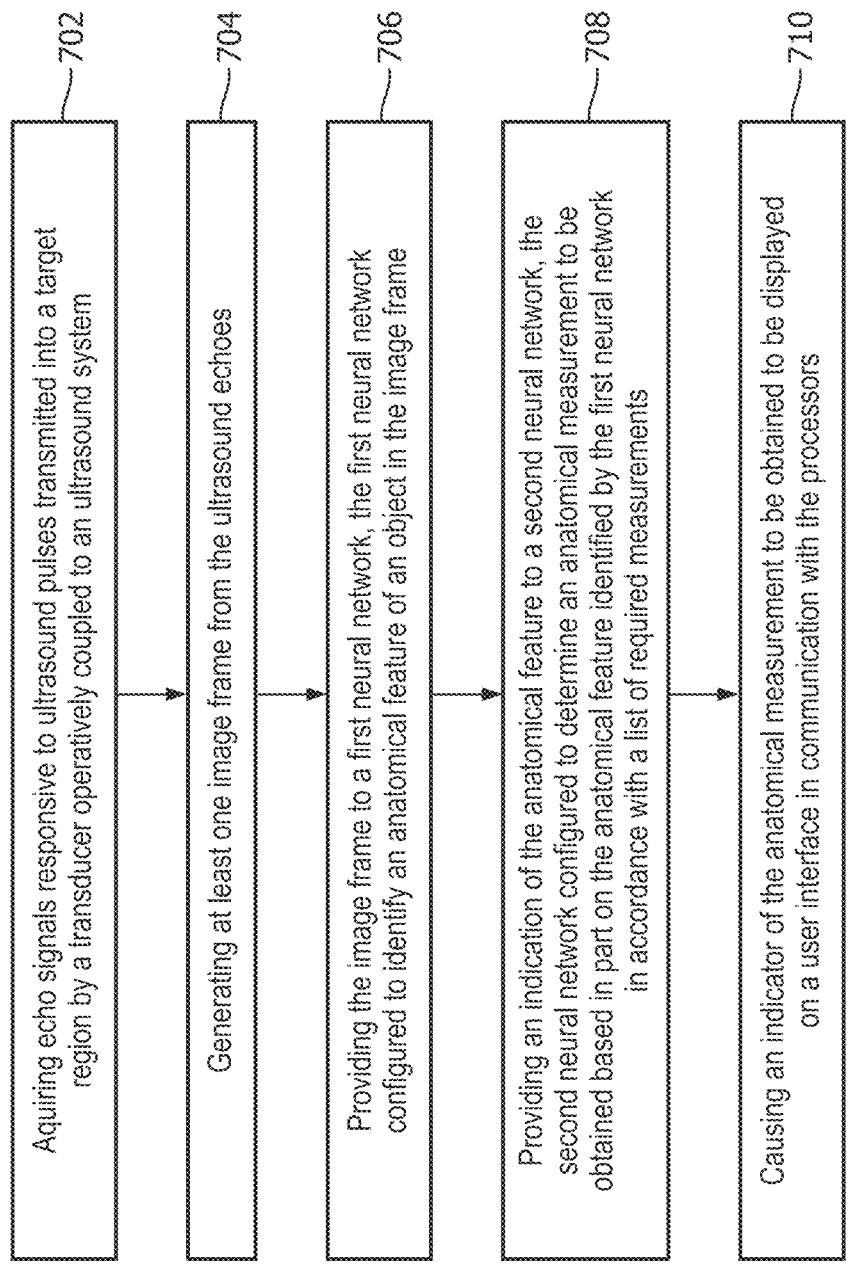
FIG. 7 is a flow diagram of a method of ultrasound imaging performed in accordance with principles of the present disclosure.

FIG. 7 is a flow diagram of a method of ultrasound imaging performed in accordance with principles of the present disclosure. The example method 700 shows the steps that may be utilized, in any sequence, by the systems and/or apparatuses described herein for determining a next measurement to be obtained during an adaptive scan protocol, which may be performed by a novice user and/or robotic ultrasound apparatus adhering to instructions generated by the system. The method 700 may be performed by an ultrasound imaging system, such as system 100, or other systems including, for example, a mobile system such as LUMIFY by Koninklijke Philips N.V. ("Philips"). Additional example systems may include SPARQ and/or EPIQ, also produced by Philips.

In the embodiment shown, the method 700 begins at block 702 by "acquiring echo signals responsive to ultrasound pulses transmitted into a target region by a transducer operatively coupled to an ultrasound system."

At block 704, the method involves "generating at least one image frame from the ultrasound echoes."

At block 706, the method involves "providing the image frame to a first neural network, the first neural network configured to identify an anatomical feature of an object in the image frame."

At block 708, the method involves "providing an indication of the anatomical feature to a second neural network, the second neural network configured to determine an anatomical measurement to be obtained based in part on the anatomical feature identified by the first neural network in accordance with a list of required measurements."

At block 710, the method involves "causing an indicator of the anatomical measurement to be obtained to be displayed on a user interface in communication with the processors."

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
    an ultrasound transducer configured to acquire echo signals responsive to ultrasound pulses transmitted toward a target region; and
    one or more processors in communication with the ultrasound transducer and configured to:
        generate at least one image frame from the ultrasound echoes;
        provide the image frame to a first neural network, the first neural network configured to identify an anatomical feature of an object in the image frame;
        provide an indication of the anatomical feature to a second neural network, the second neural network configured to determine an anatomical measurement to be obtained based, in part, on the anatomical feature identified by the first neural network in accordance with a list of required measurements; and
        cause an indicator of the anatomical measurement to be obtained to be displayed on a user interface in communication with the processors.

2. The ultrasound imaging system of claim 1, wherein the processors are further configured to generate an instruction for adjusting the ultrasound transducer based on the anatomical measurement to be obtained.

3. The ultrasound imaging system of claim 1, wherein the processors are further configured to identify a movement of the object and a current position of the object.

4. The ultrasound imaging system of claim 3, wherein the processors are further configured to provide an indication of the movement and current position of the object to the second neural network which is configured to determine the anatomical measurement to be obtained based in part on the movement and current position of the object.

5. The ultrasound imaging system of claim 3, wherein the processors are configured to identify a movement of the object by cross-correlating a subset of lines of consecutive image frames generated from the ultrasound echoes.

6. The ultrasound imaging system of claim 3, wherein the processors are configured to identify a current position of the object by extracting anatomical features from the image frame and inputting the extracted anatomical features into a recurrent neural network.

7. The ultrasound imaging system of claim 1, wherein the second neural network is configured to implement a recommender system configured to associate the anatomical feature identified by the first neural network with an action for obtaining the anatomical measurement to be obtained.

8. The ultrasound imaging system of claim 1, wherein the first neural network is operatively associated with a training algorithm configured to receive an array of training inputs and known outputs, wherein the training inputs comprise ultrasound image frames containing anatomical features of an object, and the known outputs comprise a view classification based on the anatomical features.

9. The ultrasound imaging system of claim 1, wherein the user interface is configured to display the list of required measurements.

10. The ultrasound imaging system of claim 9, wherein the user interface is configured to update the list of required measurements based in part on measurements that have been obtained by a user.

11. The ultrasound imaging system of claim 1, wherein the anatomical measurement to be obtained comprises a measurement obtainable by implementing a smallest possible adjustment of the ultrasound transducer.

12. The ultrasound imaging system of claim 1, wherein the anatomical measurement to be obtained comprises a measurement obtainable at or above an accuracy threshold.

13. A method of ultrasound imaging, the method comprising:
    acquiring echo signals responsive to ultrasound pulses transmitted into a target region by a transducer operatively coupled to an ultrasound system;
    generating at least one image frame from the ultrasound echoes;
    providing the image frame to a first neural network, the first neural network configured to identify an anatomical feature of an object in the image frame;
    providing an indication of the anatomical feature to a second neural network, the second neural network configured to determine an anatomical measurement to be obtained based in part on the anatomical feature identified by the first neural network in accordance with a list of required measurements; and causing an indicator of the anatomical measurement to be obtained to be displayed on a user interface in communication with the processors.

14. The method of claim 13, further comprising generating an instruction for adjusting the ultrasound transducer based on the anatomical measurement to be obtained.

15. The method of claim 13, further comprising identifying a movement of the object and a current position of the object.

16. The method of claim 15, further comprising providing an indication of the movement and current position of the object to the second neural network which determines the anatomical measurement to be obtained.

17. The method of claim 15, wherein identifying the movement of the object comprises cross-correlating a subset of lines of consecutive image frames generated from the ultrasound echoes.

18. The method of claim 15, wherein identifying the current position of the object comprises extracting anatomical features from the image frame and inputting the extracted anatomical features into a recurrent neural network.

19. The method of claim 13, further comprising displaying and updating the list of requirement measurements based in part on measurements that have been obtained by a user.

20. A non-transitory computer-readable medium comprising executable instructions, which when executed cause a processor of a medical imaging system to perform the methods of claim 13.

* * * * *